Figure 1:
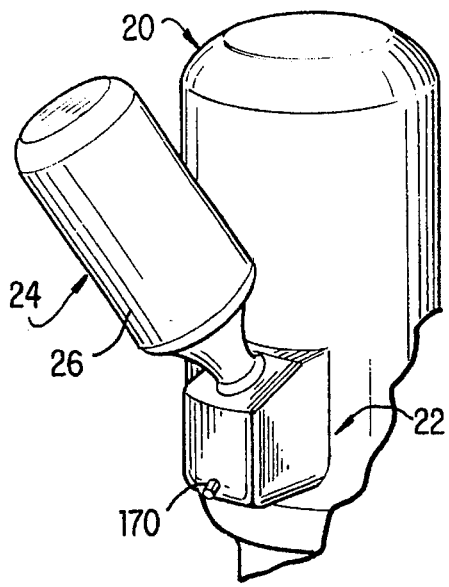

United States Patent [19]

Grabenkort et al.

[11] Patent Number: 5,505,236
[45] Date of Patent: Apr. 9, 1996

[54] ANESTHETIC VAPORIZER FILLING SYSTEM

[75] Inventors: Richard W. Grabenkort, Barrington; Peter C. Carveth, Chicago, both of Ill.; Richard J. Fiedorowicz, Abingdon; Alan C. Green, Grove, both of England; David A. Pecosky, Gurnee; William L. Rudzena, McHenry, both of Ill.

[73] Assignee: Abbott Laboratories, Abbott Park, Ill.

[21] Appl. No.: 222,768

[22] Filed: Apr. 4, 1994

[51] Int. Cl.[6] .................................................. B65B 1/04
[52] U.S. Cl. .................... 141/329; 141/382; 128/203.12; 128/202.27
[58] Field of Search .................................. 141/291, 292, 141/293, 296, 329, 357, 382; 128/202.27, 203.12

[56] References Cited

U.S. PATENT DOCUMENTS

| | | | |
|---|---|---|---|
| 1,600,549 | 9/1926 | Jurs | 141/382 |
| 2,202,459 | 5/1940 | Link | 141/382 |
| 3,115,907 | 12/1963 | Labat | 141/291 |
| 3,125,135 | 3/1964 | Boyer et al. | 141/293 |
| 3,146,808 | 9/1964 | Zellweger | 141/293 |
| 3,217,762 | 11/1965 | Burchett | 141/293 |
| 3,277,674 | 10/1966 | Klein et al. | 141/329 |
| 3,416,577 | 12/1968 | Franz | 141/293 |
| 3,799,222 | 3/1974 | Franz | 141/291 |
| 3,874,380 | 4/1975 | Baum | 141/329 |
| 4,614,437 | 9/1986 | Buehler | 141/329 |
| 4,883,049 | 11/1989 | McDonald | 128/202.22 |
| 4,893,659 | 1/1990 | Löliger | 141/329 |
| 5,170,823 | 12/1992 | Gregory et al. | 141/382 |
| 5,287,898 | 2/1994 | Falb et al. | 141/329 |
| 5,381,836 | 1/1995 | Braatz et al. | 141/292 |

FOREIGN PATENT DOCUMENTS

| | | |
|---|---|---|
| 2261201 | 9/1975 | France . |
| 1900271 | 8/1969 | Germany . |
| 4106756 | 9/1992 | Germany . |
| WO92/12752 | 8/1992 | WIPO . |
| WO93/09753 | 5/1993 | WIPO . |

*Primary Examiner*—Aaron J. Lewis
*Attorney, Agent, or Firm*—Thomas M. Breininger; Brian R. Woodworth

[57] ABSTRACT

A system is provided for the delivery of a liquid anesthetic agent ti ab anesthetic vaporizer. The system includes a supply container having a spout defining an outlet through which the agent can be discharged. A reservoir is provided in the vaporizer for holding the agent, and a receiving station is provided on the vaporizer for receiving the container spout. The agent flows from the container through the spout by gravity into the reservoir. The container spout is located at the station to define the maximum liquid level of the agent in the vaporizer when gas flow into the container is blocked by the rising level of the liquid agent. In one embodiment, a frangible seal is provided in the container, an outlet valve is provided in the container, and an inlet valve is provided in the receiving station. The valves open automatically as the container is inserted into the receiving station of the vaporizer. Also, the container spout is preferably movable relative to a collar so as to automatically effect rupture of the frangible membrane as the container is inserted into the receiving station of the vaporizer.

23 Claims, 10 Drawing Sheets

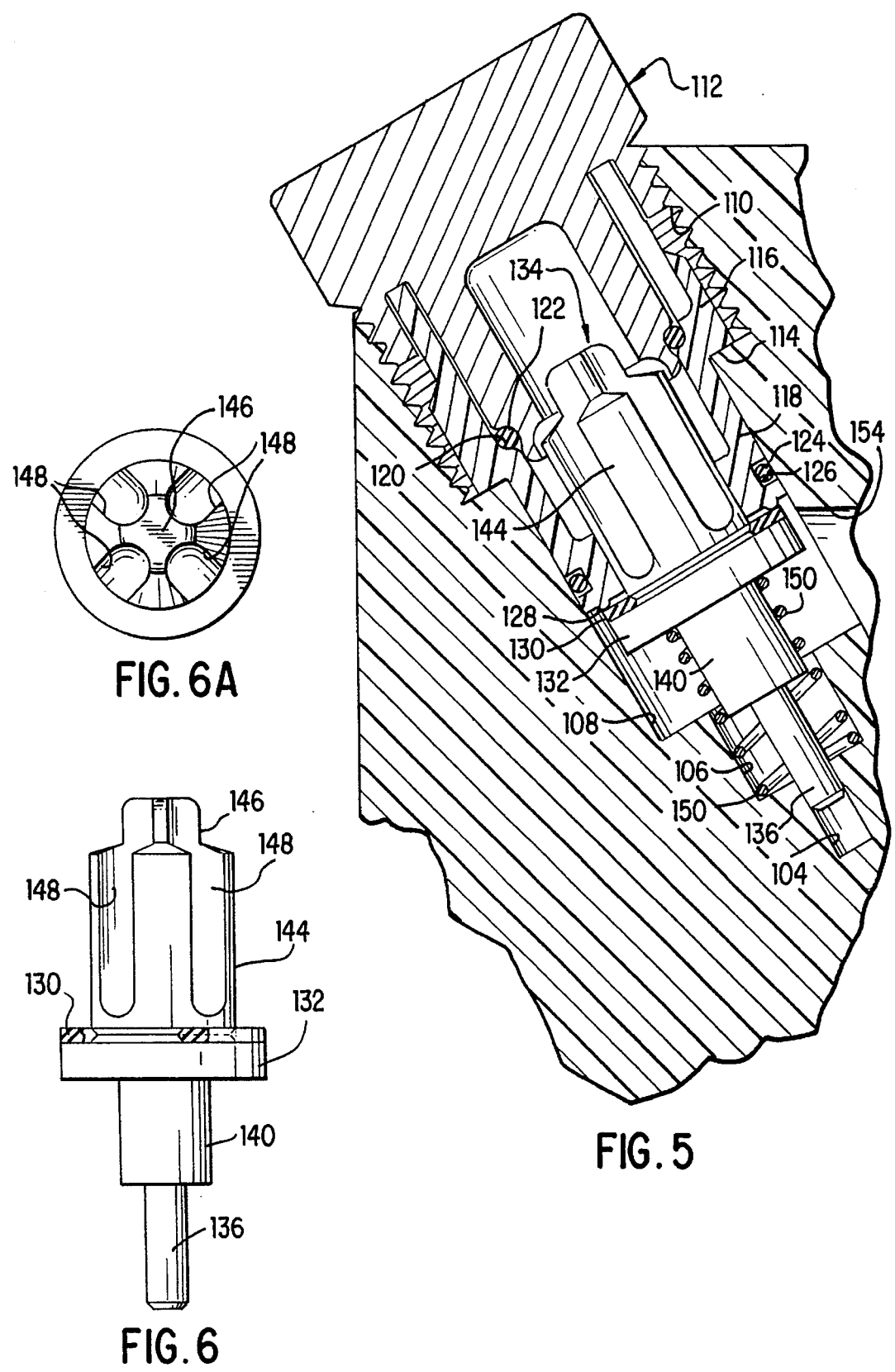

5,505,236

ANESTHETIC VAPORIZER FILLING SYSTEM

TECHNICAL FIELD

The present invention relates to a system for use in medical facilities to safely accommodate the transfer of an anesthetic agent from a container to a vaporizer for administration of the agent to a patient.

BACKGROUND OF THE INVENTION AND TECHNICAL PROBLEMS POSED BY THE PRIOR ART

Inhalable anesthetics (which are alternatively described as anesthetic agents) are typically volatile substances with relatively low boiling points and high vapor pressures. They can be flammable and explosive substances in both their liquid and vapor states. Further, inhalation of the vapor by health care personnel can cause drowsiness.

Therefore, such anesthetics must be safely handled in operating rooms in order to minimize the risk of inhalation by medical personnel as well as to minimize the risk of fire or explosion. Preferably, the anesthetic should be used in a way which will ensure that there is little or no release to the atmosphere at all stages of handling.

Anesthetics are typically dispensed in liquid form to an apparatus, such as an anesthetic vaporizer, which mixes the anesthetic with oxygen and nitrous oxide. The mixture is supplied in gaseous form to the patient for inhalation.

Devices have been designed for the transfer of an anesthetic from a supply container to a vaporizer through a closed system that minimizes the likelihood of the escape of an anesthetic gas to the atmosphere. The devices are designed so that during set-up and disassembly procedures, a supply container of anesthetic is not open and exposed to the atmosphere.

One system which has been developed for connecting an anesthetic container to a vaporizer is the SECURITY LOCK™ Vapofill vaporizer connector sold by Abbott Laboratories, Inc., One Abbott Park Road, Abbott Park, Ill. 60064-3500, U.S.A. and Abbott S.p.A., 04010 Campoverde, Latina, Italia. It may be disposable, and it employs a connector tube having special connecting or coupling members at both ends. The tube is flexible and is kink-resistant. The vaporizer end of the tube is provided with a vaporizer connector, adaptor, coupling member, or pin that engages an anesthetic vaporizer. This can be initially closed with a removable cap. The end of the tube attached to the anesthetic container is provided with a closure adaptor that engages a closure on the anesthetic container.

The closure is preferably connected to the anesthetic container prior to use. The container closure has a frangible seal adapted to be perforated by a piercing means within the closure adaptor as the adaptor engages the closure. Following perforation of the frangible seal by the piercing means, the closure adaptor and closure remain locked together, and this permits the transport of anesthetic through the tube from the supply container to the vaporizer. The system remains closed to the atmosphere throughout the assembly or disassembly procedures.

While the above-described SECURITY LOCK™ transfer system is effective in transferring a liquid anesthetic agent to the vaporizer, the operator must properly dispense the anesthetic into the vaporizer in a manner that avoids overfilling the vaporizer beyond a maximum level. This may be accomplished in various ways, such as by ascertaining the level of anesthetic, if any, existing in the vaporizer and dispensing the anesthetic from a supply container having a quantity of anesthetic that will not overfill the vaporizer. Alternatively, where a large supply of anesthetic is provided in the container, the filling process can be monitored so that the filling process can be terminated when the anesthetic in the vaporizer has reached the desired maximum level (e.g., such as can be seen on a sight glass connected to the vaporizer).

While such processes function well when properly executed, it would be desirable to provide an improved system which would be more convenient and which would eliminate the need for careful monitoring by the operator. In particular, it would be advantageous if such an improved system could provide a process for positively stopping the filling of the vaporizer at a predetermined level, regardless of the quantity of anesthetic agent in the supply container.

It would also be advantageous if such an improved system employed container components and structures that could accommodate storage of the anesthetic during a relatively long shelf life without the container structures being degraded to an extent that might deleteriously affect subsequent use of the container to fill the vaporizer.

Further, it would be desirable to provide such an improved system that can accommodate designs significantly minimizing the likelihood of spillage or leakage while at the same time accommodating a relatively rapid filling of the vaporizer.

Some types of vaporizers are intended for use with only a specific anesthetic. In such situations, care must be taken to insure that only the proper anesthetic is dispensed into the particular vaporizer. To this end, the above-discussed SECURITY LOCK™ device has been provided with a keying system to prevent the use of the device with an anesthetic for which it is not designed.

In particular, the anesthetic container closure has a specific shape, and the connector tube closure adaptor has a complementary shape for mating with the container closure. At the other end of the container tube, the pin has a special shape for mating with a complementary portion of the vaporizer anesthetic inlet port.

Vaporizer manufacturers provide standard inlet port configurations. These are standardized to I.S.O. ("International Standardization Organization") configurations specific to various types of anesthetics. Because the container for each type of anesthetic has its own special closure shape and color, and because the corresponding connector device fits only the type of vaporizer designed for that type of anesthetic, the probability of inadvertently using the wrong type of anesthetic in a vaporizer is greatly reduced.

Although such keyed, connector tubes function satisfactorily, there are inventory, installation, operation, and management requirements and considerations associated with their proper use. It would be desirable to minimize such requirements and considerations. In particular, it would be advantageous to provide a system with improved connection structures or engagement structures for minimizing the likelihood that the container can be improperly connected at the vaporizer. Such an improved system should facilitate the formation of a connection that is not susceptible to leakage of the anesthetic liquid or vapor.

The present invention provides an improved anesthetic transfer system which can accommodate designs having the above discussed benefits and features.

SUMMARY OF THE INVENTION

One aspect of the invention includes a process for facilitating the proper transfer of anesthetic from a container to a vaporizer in a way that avoids overfilling the vaporizer. In this process a container of the anesthetic agent is inverted in a receiving reservoir in the vaporizer. The container defines an outlet through which the agent can be discharged by gravity flow. The container outlet is located at the reservoir so as to define the maximum liquid level of the agent in the reservoir. When the flow of gas (e.g., ambient air) into the container is blocked by the rising level of the agent, any excess agent will remain in the inverted container and will not flow into the vaporizer reservoir.

According to a related apparatus aspect of the invention, the delivery system includes an anesthetic agent supply container defining an outlet through which the agent can be discharged. The vaporizer includes a reservoir for holding the agent. A receiving station is included on the vaporizer for receiving the container, and the agent is dispensed through the receiving station into the reservoir. The container outlet is located in the receiving station on the vaporizer so as to fill the reservoir by gravity flow and establish a predetermined maximum fill level of the vaporizer at the container outlet.

According to another aspect of the invention, an anesthetic vaporizer is also filled with a liquid anesthetic agent from a container of the agent. The method includes inverting the container of the agent and disposing the container in a receiving station or passage in the vaporizer.

In one form of the method, the container has an outlet structure including an outlet valve and a frangible membrane sealing off communication between the agent and the outlet valve. After the container is inverted in the receiving station or passage, the outlet valve is opened. Then the frangible web is ruptured so that the agent can flow by gravity into the vaporizer.

In another form of the method the container includes a hollow body containing the agent, a collar on the body, a spout mounted within the collar and movable lengthwise between (1) a retracted position and (2) an extended position, and a frangible membrane sealing the hollow body inwardly of the spout. The spout has a proximal end for engaging the frangible membrane and has a structure for engaging the receiving station to limit movement of the spout into the receiving station. The container is inverted and disposed in the receiving station and moved inwardly so that the spout engages the receiving station which limits further inward movement of the spout. The inward movement of the container and collar continues whereby the body and collar continue to move inwardly relative to the spout to carry the membrane against the spout proximal end and rupture the membrane.

According to a related apparatus aspect of the invention, the delivery system includes an anesthetic agent supply container and an anesthetic vaporizer with a receiving station for receiving the container so that the agent can be dispensed from the container. The container includes a hollow body containing the agent, a collar on the body, a spout mounted within the collar and movable lengthwise between (1) a retracted position and (2) an extended position, and a frangible membrane sealing the hollow body inwardly of the spout.

The spout has a proximal end for engaging the frangible membrane and has a structure for engaging the receiving station to limit the movement of the spout into the receiving station. Thus, the body and collar can continue to move inwardly relative to the spout so that the membrane carried against the spout proximal end is ruptured by the spout proximal end.

According to another aspect of the invention, a delivery system for delivery of liquid anesthetic agent to an anesthetic vaporizer includes an anesthetic agent supply container defining an outlet through which the agent can be discharged. A valve seat as provided in the container. A valve member is provided in the container and is biased toward a closed position against the seat whereby flow through the outlet is occluded. A cap is removably attached to the container. The cap engages the valve member and holds the valve member away from the seat to prevent contact between the valve seat and valve member prior to removal of the cap.

Another aspect of the invention includes a delivery system for delivery of a liquid anesthetic agent to an anesthetic vaporizer wherein an anesthetic agent supply container is provided with an outlet through which the agent can be discharged. A valve member is provided in the container along with a first spring biasing the outlet valve member to an extended, closed position occluding flow through the outlet. A receiving station is provided on the anesthetic vaporizer for receiving the container. The agent can be dispensed from the container into the receiving station when the outlet valve member is opened.

A movable engaging member is provided in the vaporizer receiving station along with a second spring for biasing the engaging member to an extended position from a fully depressed position. The engaging member is engagable with the outlet valve member and is urged to the fully depressed position when the container is inserted into the vaporizer receiving station. The engaging member is restrained in the fully depressed position against further movement away from the extended position. The second spring has less compression force than the first spring so that the outlet valve member is moved away from the closed position by the engaging member in the receiving station only after the engaging member has been urged to the fully depressed position.

In a presently preferred embodiment, the frangible membrane can be eliminated. The outlet valve includes a sealing cap for effecting a leak-tight seal against the outlet valve seat. Preferably, the sealing cap is fabricated from low density polyethylene and is snap-fitted to a receiving structure. Further, rather than incorporate a movable spout, the preferred embodiment of the container includes a stationary spout which is internally threaded for threadingly engaging an overcap. After the overcap is removed, the container can be inverted in the receiving station of the vaporizer, and the outlet valve is opened in response to engagement with an inlet valve, or other engaging member, in the receiving station. The maximum fill level of the vaporizer can be established by the outlet of the fixed spout in substantially the same manner that the maximum fill level is established as described above with respect to the blockage of a container outlet by the rising level of the liquid agent.

In an alternate process for filling a vaporizer, a funnel may be employed with a conventional container. The funnel can be inserted into the vaporizer receiving station to open the inlet valve while the liquid agent is discharged from the container through the funnel, through the open inlet valve, and into the vaporizer.

Another aspect of the invention relates to a keying configuration in a delivery system for delivery of a liquid anesthetic agent to an anesthetic vaporizer. The system includes a reservoir in the vaporizer for holding the agent and a receiving station on the vaporizer. The vaporizer has a wall defining a generally cylindrical passage through which the agent can flow by gravity into the reservoir. The station wall defines at least one groove longitudinally oriented to, and communicating with, the passage.

An elongate conduit structure is provided for being received in the receiving station passage to direct a flow of the agent from a supply exterior of the station into the vaporizer. The conduit structure may be integral with the container and may define part of a collar or spout on the container. Alternatively, the conduit structure could include the spout of a funnel.

The conduit structure defines at least one rib. The receiving station has a groove which is adapted to receive the rib whereby the conduit structure can be oriented to effect alignment of the rib and groove to permit the conduit structure to be inserted into the receiving station.

Preferably, a plurality of ribs and grooves are employed. If desired, the ribs may instead be provided on the receiving station while the conduit structure may include the grooves. The use of the rib and groove feature permits the vaporizer and conduit structure to be designed for use together with a specific anesthetic agent.

Finally, another aspect of the invention relates to a novel outlet design for a container used as part of a delivery system for delivery of liquid anesthetic agent to an anesthetic vaporizer which has a receiving station with an engaging member projecting in the direction outwardly of the station. The container defines an outlet through which the agent can be discharged. The container defines an outlet valve seat at the outlet. The container includes an outlet valve biased toward the seat. The outlet valve defines a non-planar sealing surface for engaging the seat when the inlet valve is closed. The outlet valve is openable by engagement with the engaging member in the vaporizer. Preferably, the outlet valve includes a sealing cap for engaging the outlet valve seat.

In a preferred embodiment, the outlet valve includes a sealing cap for engaging the outlet valve seat, and the sealing cap has a peripheral, outwardly convex, arcuate sealing surface. The outlet valve seat is defined by an inwardly concave, arcuate surface.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a fragmentary, perspective view of the delivery system for delivery of a liquid anesthetic agent to an anesthetic vaporizer in accordance with the principles of the present invention, and FIG. 1 shows an anesthetic agent supply container inverted and mounted in a receiving station of an anesthetic vaporizer;

FIG. 2 is a greatly enlarged, fragmentary, cross-sectional view of the container in an upright position and in a sealed condition with an overcap installed thereon to hold an outlet valve open;

FIG. 3 is a fragmentary, cross-sectional view taken generally along the plane 3—3 in FIG. 2;

FIG. 4 is a view similar to FIG. 2, but shows the container after the overcap has been removed and the outlet valve has closed;

FIG. 5 is a greatly enlarged, fragmentary, cross-sectional view of the receiving station portion of the vaporizer with a removable stopper therein;

FIG. 6 is a side elevational view of a combined engaging member and outlet valve structure which is mounted in the vaporizer receiving station;

FIG. 6A is a top plan view of the assembly shown in FIG. 6;

FIG. 7 is a view similar to FIG. 5, but shows the stopper removed and the uncapped container of FIG. 4 inverted and partially inserted into the receiving station of the vaporizer;

FIG. 8 is a fragmentary, cross-sectional view taken generally along the plane 8—8 in FIG. 7;

FIG. 9 is a view similar to FIG. 7, but FIG. 9 shows the container inserted further into the vaporizer receiving station;

FIG. 10 is a fragmentary, cross-sectional view taken generally along the plane 10—10 in FIG. 9;

FIG. 11 is a view similar to FIG. 9, but FIG. 11 shows the container inserted further into the vaporizer receiving station;

FIG. 12 is a view similar to FIG. 11, but FIG. 12 shows the container fully inserted into the vaporizer receiving station;

FIG. 13 is a fragmentary, cross-sectional view of a preferred, alternate embodiment of the container in an upright position and in a closed condition with an overcap installed thereon;

FIG. 14 is a perspective view of the plunger of the container shown in FIG. 13;

FIG. 15 is a fragmentary, perspective view showing another form of the method of the present invention for filling a vaporizer;

FIG. 16 is a view similar to FIG. 12, but illustrating the alternate form of filling the vaporizer as shown in FIG. 15; and FIGS. 17–19 are transverse cross-sections illustrating alternative keying embodiments that may be employed with the vaporizer and container collar, spout, or other conduit employed for directing flow from a supply container into the vaporizer.

DESCRIPTION OF THE PREFERRED EMBODIMENTS

The present invention provides a novel system which includes processes and apparatus for connecting an anesthetic container to a vaporizer and filling the vaporizer. The system can be provided in a number of different designs incorporating a variety of different features and capabilities.

According to one aspect of the invention, the system includes means for connecting the anesthetic container to the vaporizer with improved engaging structures, supporting structures, valving structures, and sealing structures.

According to another aspect of the invention, the system permits the vaporizer to be relatively quickly filled by gravity and prevents the vaporizer from being overfilled.

The system can include a sealed container which can be automatically opened as the container is mounted on the vaporizer. A dynamic O-ring system is not required, yet leakage and spillage is avoided or minimized.

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

For ease of description, the system components of this invention are described in the normal storage and operating positions, and terms such as upper, lower, horizontal, etc., are used with reference to these positions. It will be understood, however, that the components of this invention may be manufactured, stored, transported, and sold in an orientation other than the positions described.

Figures illustrating the components of the invention show some mechanical elements that are known and that will be recognized by one skilled in the art. The detailed descriptions of such elements are not necessary to an understanding of the invention and, accordingly, are herein presented only to the degree necessary to facilitate an understanding of the novel features of the present invention.

A portion of the vaporizer which can be filled according to the principles of the present invention is illustrated in FIG. 1 and is designated therein by reference number 20. The vaporizer 20 includes a receiving station 22 for receiving an anesthetic agent supply container 24. Except for the receiving station 22, the structure and operation of the vaporizer 20 may be of any conventional or special design, the details of which form no part of the present invention.

The container 24 includes a body or body portion 26 which includes a neck 28. The body portion 26 contains the liquid anesthetic agent, and when the container 24 is inverted and opened (in a manner described in detail hereinafter), the liquid agent flows by gravity into the receiving station 22 to fill a reservoir within the vaporizer 20.

Mounted to the top of the container neck 28 is a gasket 30, a frangible membrane insert 32 having a flange 34 disposed on the gasket 30, and an indexing collar 36 having a flange 38 disposed on top of the membrane insert flange 34. Mounted within the collar 36 is a movable spout 40. A metal ferrule 39 is crimped around the top of the container neck, gasket 30, insert 32 and collar flange 38 to hold the assembly together.

A removable cap 42 is mounted over the spout 40 and is secured to the collar 36. To this end, the collar 36 defines an annular groove 44, and the lower, inside peripheral edge of the cap 42 defines an annular bead 46 for establishing a snap-fit engagement with the groove 44.

The frangible membrane insert 32 covers the container opening defined by the neck 28 and includes a generally disk-like frangible membrane 50. The insert 32 is sealingly mounted within the container neck 28 so as to seal the liquid anesthetic agent A within the container body 26. The frangible membrane 50 can be ruptured or broken away around its periphery, by means described in detail hereinafter, in order to permit the agent A to be dispensed.

Typically, the membrane is molded as a unitary part of the insert 32 from a suitable thermoplastic polymer material. A peripheral, annular region around the edge of the membrane 50 may be defined by a reduced thickness section of material to assist in providing a preferential rupture or break locus.

The container body 26 and neck 28 may be fabricated from suitable materials, such as glass or thermoplastic materials, which are compatible with the anesthetic agent. The collar 36 and spout 40 are also preferably fabricated from thermoplastic materials compatible with the anesthetic agent.

Similarly, the cap 42, which never comes in contact with the anesthetic agent, may be fabricated from a suitable thermoplastic material having sufficient resilience to accommodate the snap-fit engagement mounting on the container.

Figure 3:
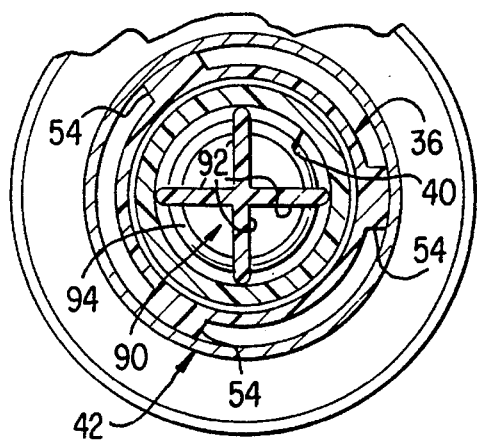

The collar 36 has three, circumferentially spaced, longitudinally oriented ribs 54 (FIG. 3). These ribs 54 function as keys and are adapted to be received in mating recesses of the vaporizer receiving station as described in detail hereinafter. The size, shape, and spatial orientation of the ribs may be established for a particular anesthetic agent supplied in the container 24. Other anesthetic agents would be provided in containers having a different rib arrangement. The rib arrangement is thus agent-specific, and will permit the insertion of a specific agent container in only a specific vaporizer designed for that container and anesthetic agent.

The spout 40 has a proximal end adjacent the membrane 50, and the proximal end defines cutting edge 58 which is oriented at an oblique angle relative to the longitudinal axis of the container 24 and to the plane of the membrane 50. The cutting edge 58 has a circular configuration and is adapted to sever, rupture, or otherwise break the membrane 50 at least partially around its peripheral edge so as to separate at least a portion of the membrane from the remaining portion of the insert 32 when relative movement is effected between the spout 40 and the membrane 50 as is described in detail hereinafter.

The spout 40, in the region adjacent the frangible membrane insert 32, defines an annular groove 62 for engaging an adjacent, annular shoulder 64 of the insert 32. The spout 40 is held by the insert shoulder 64 so that the spout cutting edge 58 is spaced away from the membrane 50. The engagement between the spout recess 62 and the insert shoulder 64 is not tightly fitting and leak-tight so as to minimize the possibility that the engaging portions will become cold formed and adhered together during a long shelf life.

The exterior of the spout 40 defines a plurality of annular ratchet teeth 70. The distal end of the collar 36 defines an annular engaging tooth 72 for engaging the ratchet teeth 70 of the spout 40. The teeth 70 and tooth 72 are configured in the well-known manner to permit movement of the tooth 72 distally along the teeth 70 (or alternatively, to permit movement of the teeth 70 proximally along the tooth 72). However, movement in the reverse direction is not possible.

The spout 40 defines an outwardly extending, annular flange 78 at the distal end of the array of teeth 70 for engaging the distal end of the collar 36 to limit movement of the collar 36 beyond the flange 78 during use of the container as explained in detail hereinafter.

A spring retaining ring 80 is mounted at a fixed location on the inside of the spout 40 just inwardly of the proximal end of the spout. The ring 80 has an outwardly projecting annular flange 82, and the inside surface of the spout 40 defines an annular groove 84 for receiving the flange 82.

The ring 80 defines a bore 86 which receives a plunger 90. The plunger 90 has a cross-shaped axial cross-section as shown in FIG. 3. The plunger comprises four walls 92 and the lower portions of the walls 92 are slidably received within the bore 86 of the ring 80. The upper portions of the walls 92 extend radially outwardly further then the lower portions of the walls and engage the inside cylindrical surface of the spout 40.

A first, compression spring 94 is mounted around the lower portions of the plunger walls 92. The lower end of the spring 94 bears against the ring 80. The upper end of the spring 94 bears against the underside of the outwardly extending upper portions of the walls 92.

Figure 4:
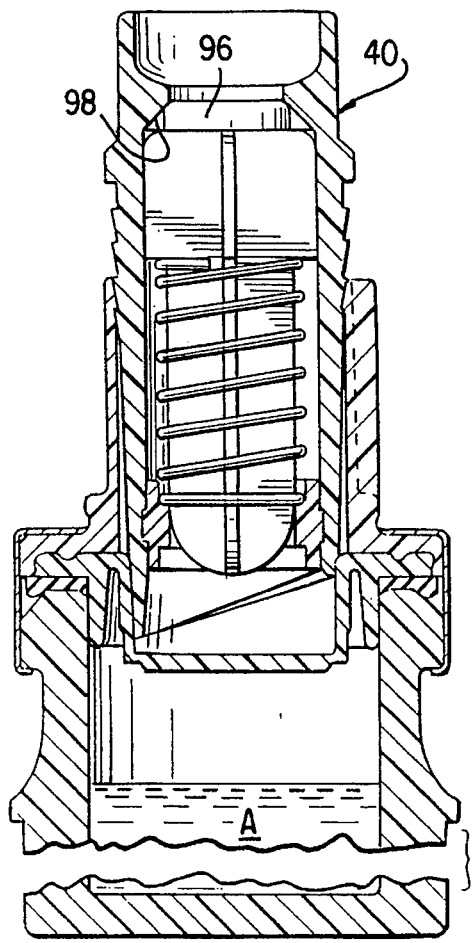

The spring 94 functions to urge the plunger 90 upwardly to a fully extended, or closed position (FIG. 4). The top of the plunger 90 incorporates a disk-like, outlet valve member 96 for sealing closed the interior of the spout 40. The distal end of the spout 40 defines an inwardly projecting annular flange defining an outlet valve seat 98. The spring 94 functions to bias the outlet valve member 96 toward a closed position sealing against the outlet valve seat 98.

The container of liquid anesthetic agent may have a relatively long shelf life. Before the container is used to fill a vaporizer, the container may sit in storage for a number of months. During this time, the container materials, especially thermoplastic polymer materials, could undergo creep or cold flow and become slightly distorted and/or locked together when subjected to continuous compressive forces. To avoid such effects on the outlet valve member 96 and outlet valve seat 98, the outlet valve member 96 is held away from the outlet valve seat 98 when the container is in storage. This is effected by the removable cap 42 which is initially installed during the manufacture of the filled container 24.

Figure 2:
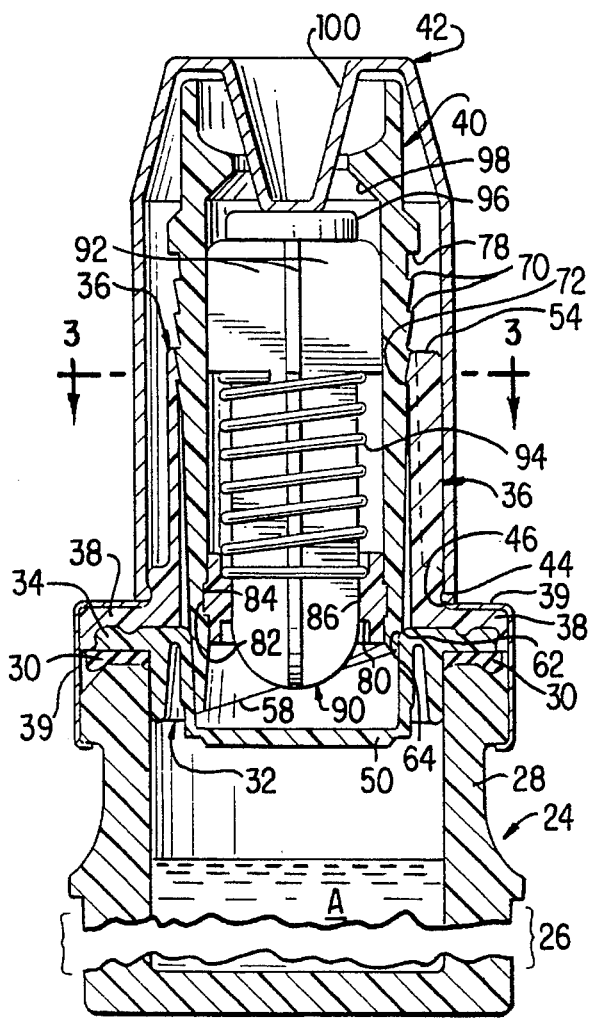

As illustrated in FIG. 2, the upper end of the cap 42 includes a downwardly projecting, frustoconical bearing structure 100. The bearing structure 100 engages the outlet valve member 96. When the cap 42 is mounted in snap-fit engagement to the base of the collar 36 as illustrated in FIG. 2, the spring 94 is somewhat compressed, and the valve member 96 is held in a position spaced inwardly of the outlet valve seat 98.

Figures 7, 8:
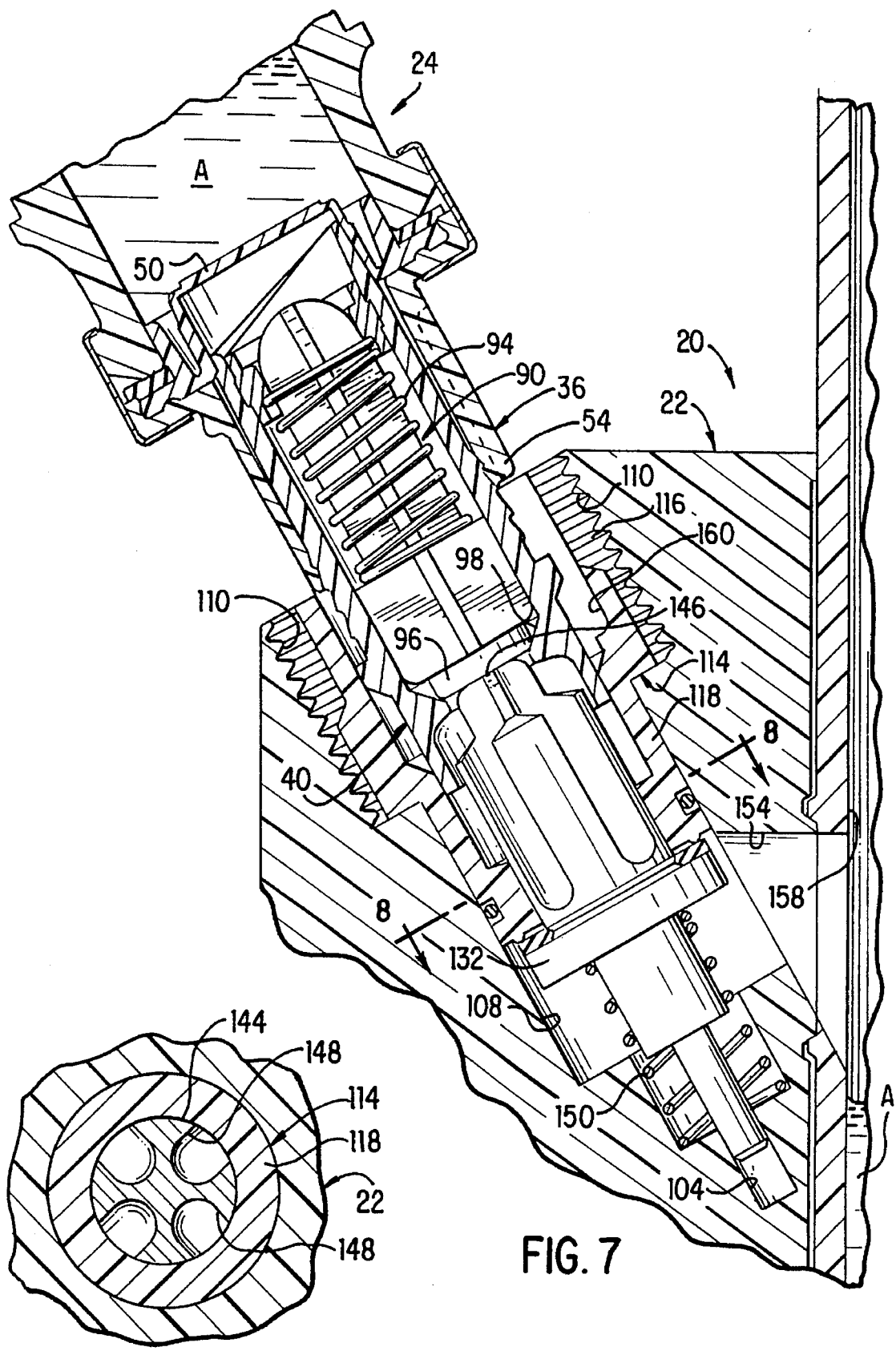

When an operator desires to use the container 24, the cap 42 is initially removed. The spring 94 then causes the valve member 96 to seat tightly against the outlet valve seat 98. Subsequently, the container 24 is inverted and disposed in the receiving station 22 of the vaporizer. As illustrated in FIGS. 5 and 7, the receiving station 22 includes an inlet passage, well, or sump which comprises a lowermost or first bore 104, a larger diameter second bore 106, a still larger diameter bore 108, and an outermost, threaded bore 110. A threaded stopper 112 (FIG. 5 only) is preferably provided for sealing the vaporizer receiving station 22 closed when the vaporizer is not being filled with anesthetic agent from a container 24.

A fixed insert sleeve 114 is mounted in the receiving station 22 inwardly of the stopper 112. The sleeve 114 has a large diameter portion 116 received in the threaded bore 110 and has a smaller diameter portion 118 received in the bore 108. The sleeve 114 defines an inner, frustoconical sealing surface 120 for being engaged by an O-ring 122 mounted at the distal end of the stopper 112. The sleeve portion 116 defines three grooves 160 for receiving the ribs 54 of the container collar 36 when the container is inserted in the vaporizer receiving station.

An O-ring 124 is mounted in a groove 126 in the exterior of the smaller diameter portion 118 of the sleeve 114 to seal against the cylindrical wall of the bore 108. The inner end of the sleeve smaller diameter portion 118 defines a projecting, annular sealing ring 128 for engaging a sealing gasket 130 mounted to the outer surface of an inlet valve member 132.

The inlet valve member 132 is preferably formed as a unitary part of an engaging member 134 which includes a pin 136 at its inner end received in the innermost bore 104. The engaging member 134 includes a cylindrical portion 140 extending between the pin 136 and the inlet valve member 132. Extending outwardly from the middle of the inlet valve member 132 is the distal end of the engaging member which includes a fluted portion 144 terminating in a smaller diameter, fluted, engaging boss 146. The boss 146 and portion 144 define four, vertically oriented, grooves or channels 148 which accommodate fluid flow as described in detail hereinafter.

A second compression spring 150 is disposed in the bores 106 and 108. The upper end of the spring 150 bears against the annular underside of the inlet valve member 132. The bottom end of the spring 150 bears against the bottom annular surface of the bore 106. The second spring 150 thus biases the inlet valve member 132 outwardly toward a closed position sealing against the stationary sleeve ring 128 (as shown in FIG. 5).

As shown in FIG. 7, the bore 108 communicates through an aperture or slot 154 defined in the receiving station 22 with a tank 158 that holds a quantity of the anesthetic agent A. The tank 158, slot 154, and bores 104, 106, and 108 together define the internal reservoir for receiving the liquid anesthetic agent from the container 24 and holding it in the vaporizer.

When it is desired to fill the vaporizer 20 with more liquid anesthetic agent A, the container cap 42 is removed from the container 24, and the container 24 is inverted and disposed within the receiving station 22 as illustrated in FIG. 7. Initially, the distal end of the container collar 36 is located just outside of the receiving station 22. The spout 40 extends into the receiving station threaded bore 110. The spout outlet valve member 96 is sealed against the outlet valve seat 98 and is closely adjacent the distal end of the engaging member boss 146. The engaging member 146 and hence, the inlet valve member 132, are at the outermost or extended positions with the valve member 132 sealing the inlet closed.

Next, the operator rotates the container 24 as necessary to align the three collar key ribs 54 with the mating, receiving recesses or grooves 160 defined around the interior of the sleeve upper portion 116. Then the container 24 can be inserted further into the receiving station 22 as shown in FIG. 9.

The second spring 150 is weaker than the first spring 94. Thus, the container outlet valve member 96 urges the receiving station inlet valve member 132 away from the inlet valve seat 128 until the pin 136 engages the bottom of the first bore 104. The container outlet valve member 96 remains closed as the inlet valve opens. Preferably, the frictional engagement between the container sleeve tooth 72 and the engaged spout teeth 70 is sufficient to prevent relative movement between the collar 36 and spout 40 while the second spring 150 compresses during this stage of the insertion process.

Figures 9, 10:
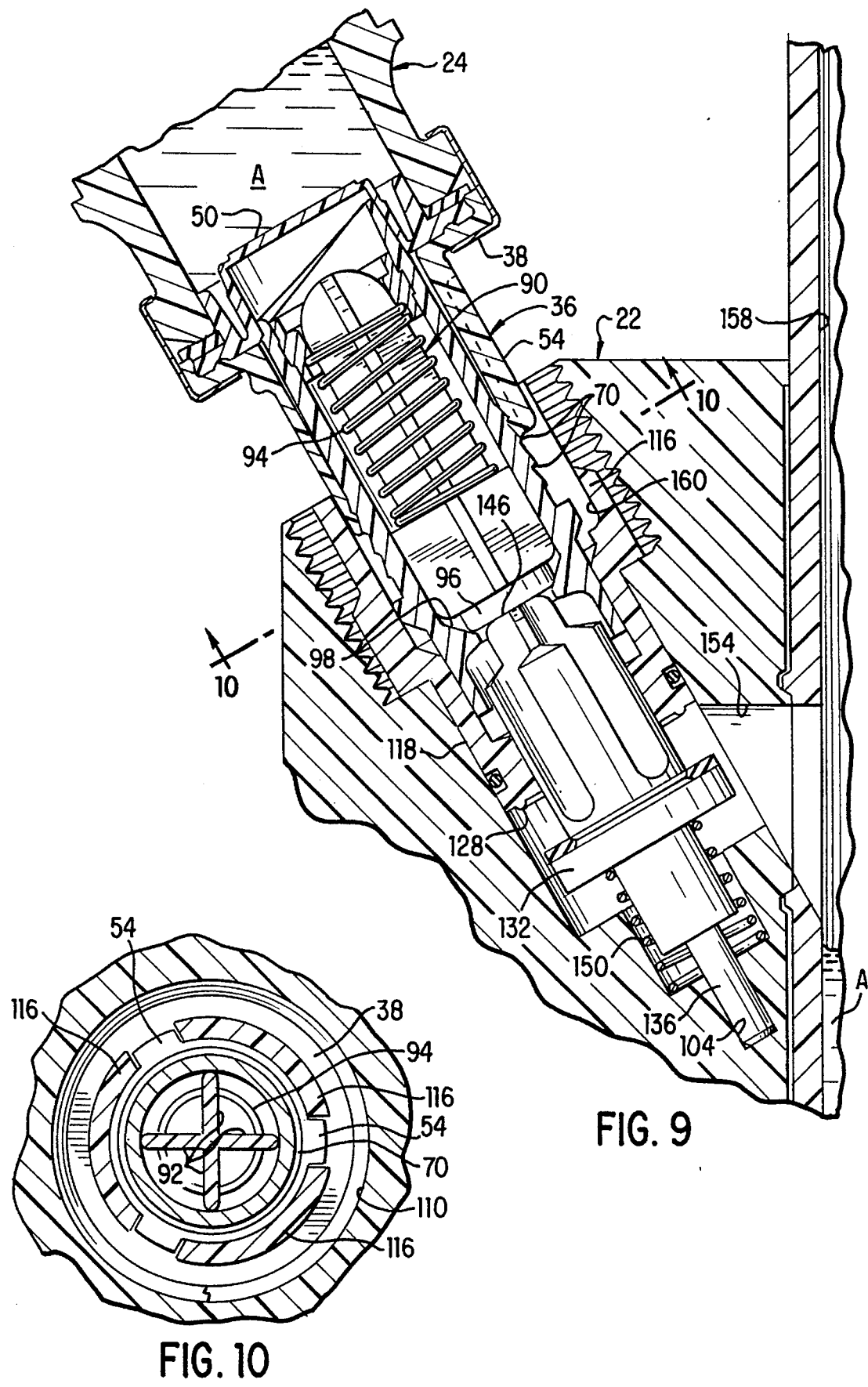
Figure 11:
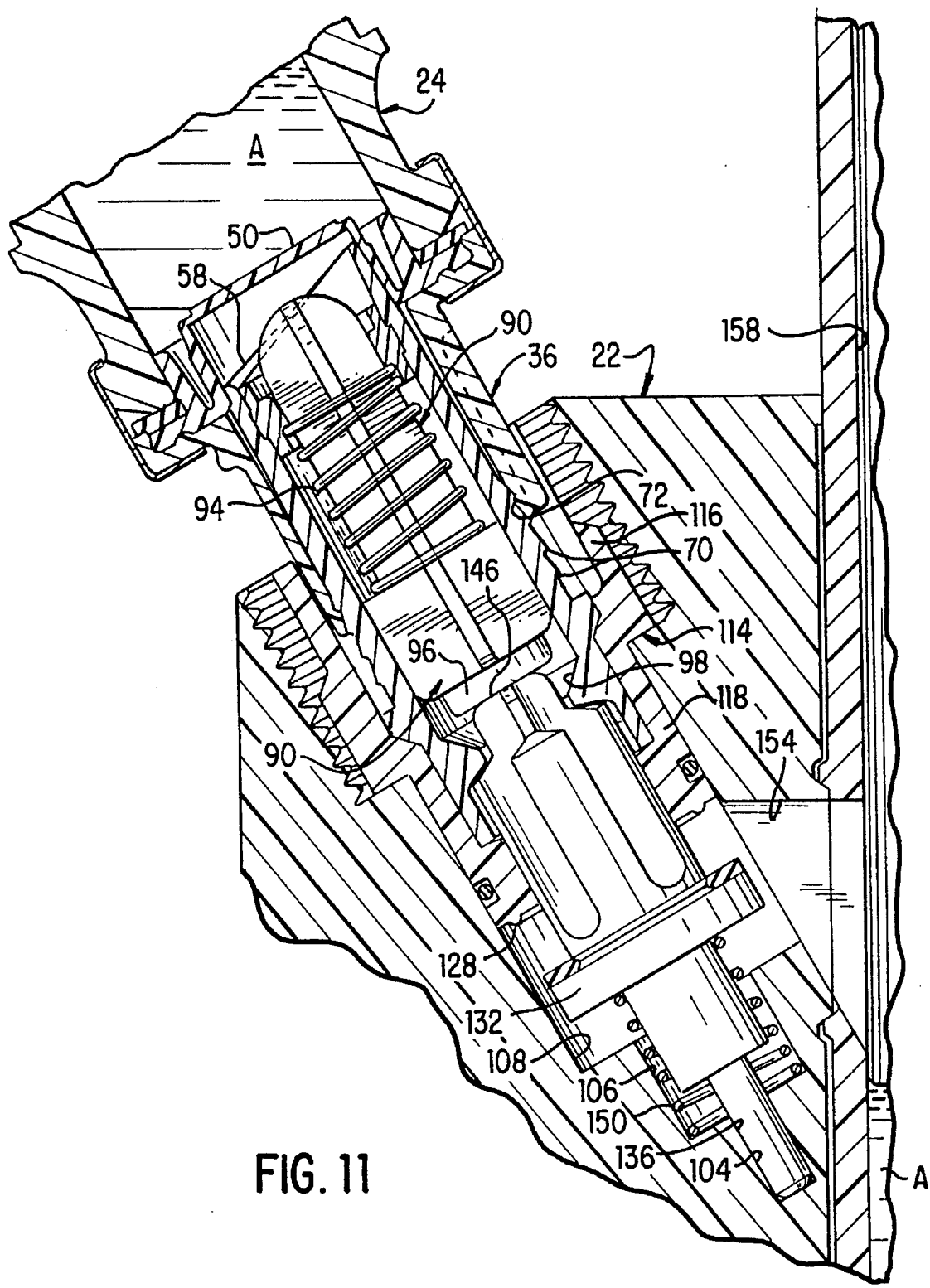

Continued insertion of the container, beyond the point illustrated in FIG. 9, causes the distal end of the spout 40 to abut the inside bottom end of the lower portion 118 of the stationary sleeve 114 as illustrated in FIG. 11. The frictional engagement between the spout 40 and the surrounding container collar 36 is sufficient to prevent relative movement so that the first spring 94 must compress as the container 24, collar 36, and spout 40 move further inwardly to the position illustrated in FIG. 11 while the plunger 90, and outlet valve member 96 carried thereon, are restrained against further inward movement by the engaging boss 146. The outlet valve member 96 thus opens, after the inlet valve member 132 has opened, but the frangible membrane 50 is still in place sealing the liquid agent A within the container body.

Subsequently, further inward movement of the container 24 and collar 36 can be accommodated only by moving the container in collar 36 inwardly relative to the spout 40 which is prevented from further inward movement by the engagement of the distal end of the spout with the stationary sleeve portion 118 in the receiving station 22. The collar 36 thus slides inwardly along the spout 40, and the collar tooth 72 moves inwardly along the spout ratchet teeth 70. It is not possible to pull the collar 36 outwardly relative to the spout 40 during this process because of the one-way engagement relationship between the collar tooth 72 and the spout teeth 70.

Figure 12:
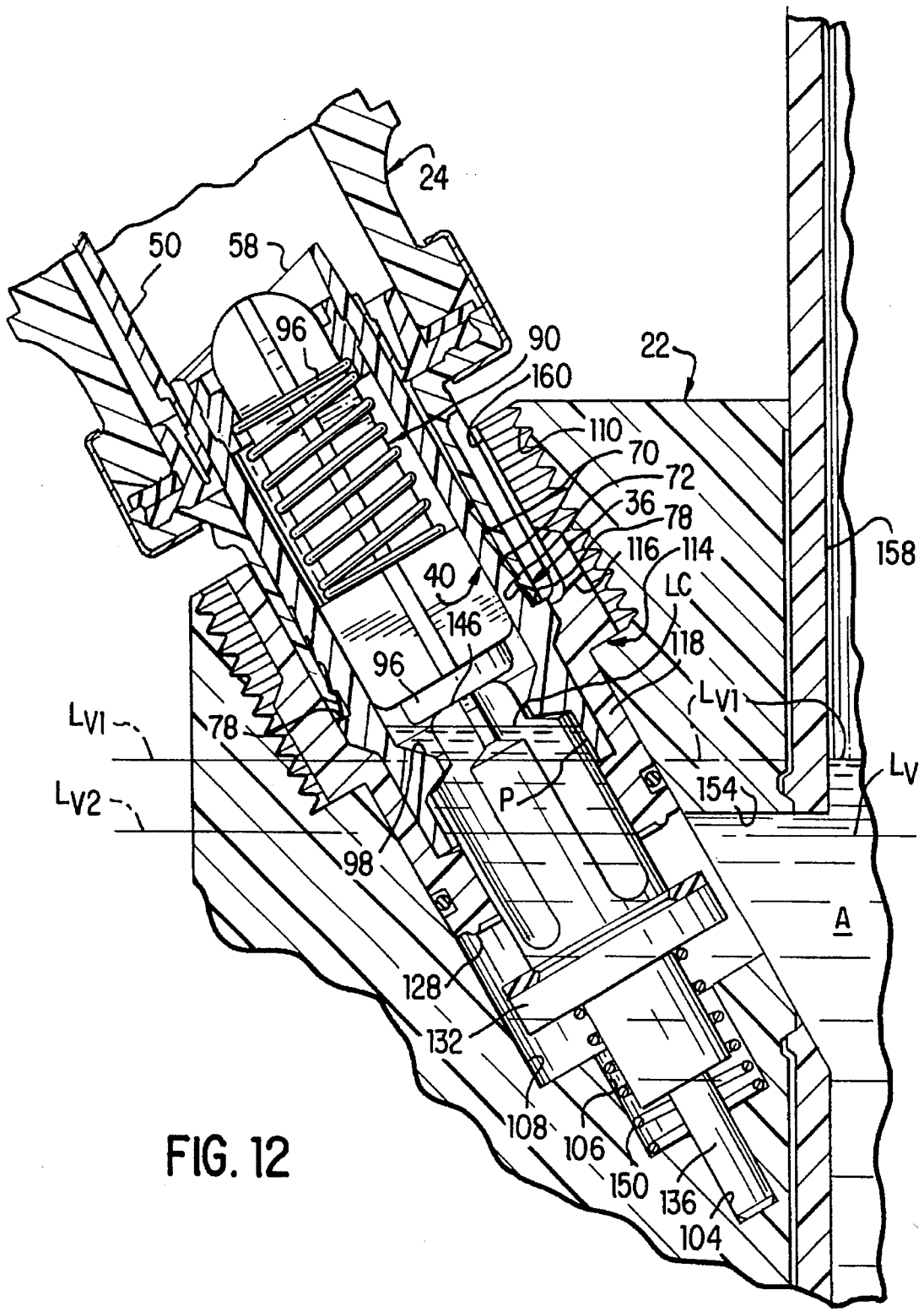

As the container 24 and collar 36 move further inwardly, the spout 40 remains stationary with its distal end abutting the sleeve portion 118. However, the frangible membrane 50 is carried by the container 24 against the cutting edge 58 at the proximal end of the spout 40. The cutting edge 58 cuts through at least a portion of the periphery of the frangible membrane 50 and pushes the frangible membrane 50 to the side as illustrated in FIG. 12. Further inward movement of the container 24 and collar 36 is prevented when the distal end of the collar 36 abuts the flange 78 on the spout 40.

As the container 24, and membrane insert 32 carried therewith, move inwardly relative to the spout 40, the proximal end of the spout adjacent the cutting edge 58 moves off of the insert shoulder 64 and forms a leak-tight seal with the insert 32 just inwardly of the frangible membrane 50. Thus, when the frangible membrane 50 is ruptured, the liquid agent cannot leak along the outside of the spout 40. The agent flows through the interior of the Spout 40 and out through the open outlet valve member 96. The agent continues to flow by gravity out of the spout 40, through the bore in the stationary sleeve 114, through the open inlet valve member 132, and through the aperture 154 into the tank 158. In some types of vaporizers, the tank 158 is vented to accommodate flow into the tank.

The liquid agent is discharged from the container 24 because pressure-equalizing ambient air can flow into the container through a special clearance path or passage. In particular, the outside surface of the distal end of the spout 40 is only loosely disposed within the surrounding sleeve 114. As shown in FIG. 12, ambient air can enter the receiving station 22 along the grooves 160 and enter the clearance space between the outside surface of the spout 40 and the adjacent stationary sleeve 114 at the bottom of the grooves 160. The ambient air then flows around the outside distal end of the spout 40 and into the outlet region of the spout 40.

As liquid agent flows out of the spout 40 under the force of gravity, the ambient air flows in. Eventually the liquid level of the agent A in the reservoir (as defined by the vented tank 158 and by the communicating passages and bores) rises to a point just covering the inside distal edge of the spout outlet at the highest point as designated by the letter P in FIG. 12.

When the clearance between the end of the spout 40 and the stationary sleeve 114 is just covered with the liquid agent A at point P, air can no longer flow through the spout into the container. This blockage of the air prevents further equalization of the pressure within the container 24. Thus, any liquid agent remaining in the container is prevented from draining out owing to the pressure differential that would result (i.e., a given ambient pressure of the liquid agent at the level $L_{v1}$ and a reduced pressure tending to be created within the container above the liquid agent). The remaining liquid agent A in the container is indicated as having a level $L_c$ in FIG. 12.

If the tank 158 was not vented to atmosphere, then, owing to the extending lower portion of the stationary sleeve 114, the level of the agent A within the tank 158 would not be able to rise above the level $L_{v2}$ as illustrated in FIG. 12. However, in any case, the maximum level that could possibly obtain for a vented or non-vented tank 158 would be the level $L_{v1}$ defined by the highest point P of the lower edge of the spout outlet.

With the novel system of the present invention, the operator can insert the container into the receiving station and need only hold the container down on the vaporizer during the filling operation. The vaporizer will be automatically filled relatively rapidly to the maximum level as predetermined by the innermost location of the highest point of the spout outlet.

If the operator wishes to subsequently remove the container 24, the engagement of the collar tooth 72 with the spout teeth 70 will cause the spout to be pulled out of the receiving station. As the spout is pulled out, the container outlet valve member 96 will close (the container first spring 94 being stronger than the receiving station spring 150). Subsequently, as the spout is pulled further outwardly, the receiving station valve member 132 will close. If there is any liquid agent left in the container, inwardly of the closed valve member 96, that liquid agent will be, of course, sealed within the closed container. A small quantity of liquid agent would then remain above the closed receiving station valve member 132, but that could be sealed within the receiving station by replacing the stopper 112 (FIG. 5).

If desired, the container 24 may be configured for threaded engagement in the receiving station 22. Also, the system may be provided with an optional drain, having a removable cap 170 (FIG. 1), communicating with the bores or passages in the receiving station. This provides an alternate drain path for draining that portion of the system.

It will be appreciated that the container 24 need not be provided as an integral structure which includes an attached collar 36 and spout 40. In a contemplated alternate embodiment, the outlet structure, such as the spout, may be provided as a separate element. The separate spout may be provided along with the container in a kit to be delivered to the medical facility. Alternatively, the spout may be provided separately at the medical facility for use with separately provided containers. Preferably, the spout and container are adapted to fit together with sufficient engagement to facilitate ease of handling, to accommodate insertion into the receiving station of the vaporizer, and to permit flow of the liquid agent from the container body through the spout and into the vaporizer.

Figure 13:
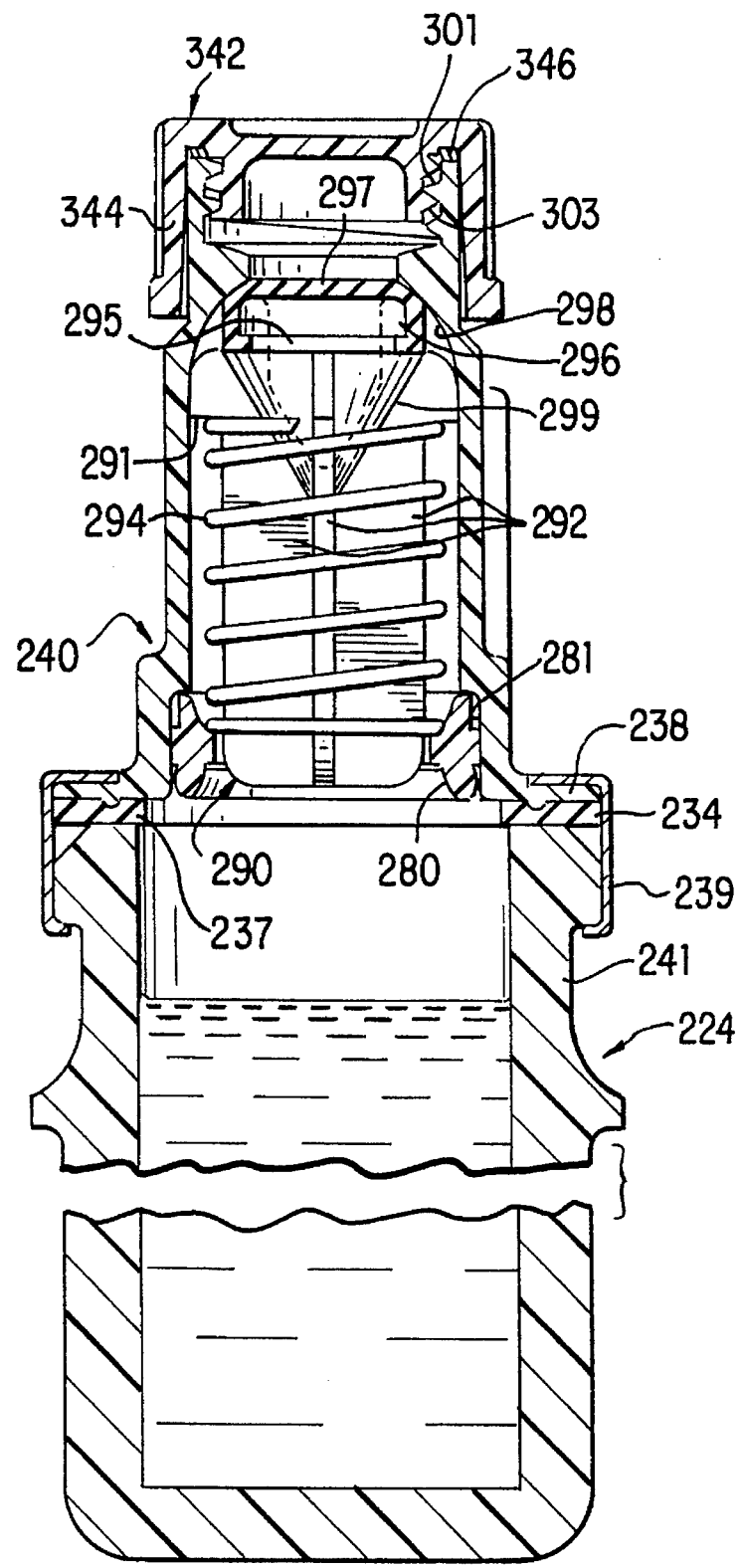
Figure 14:
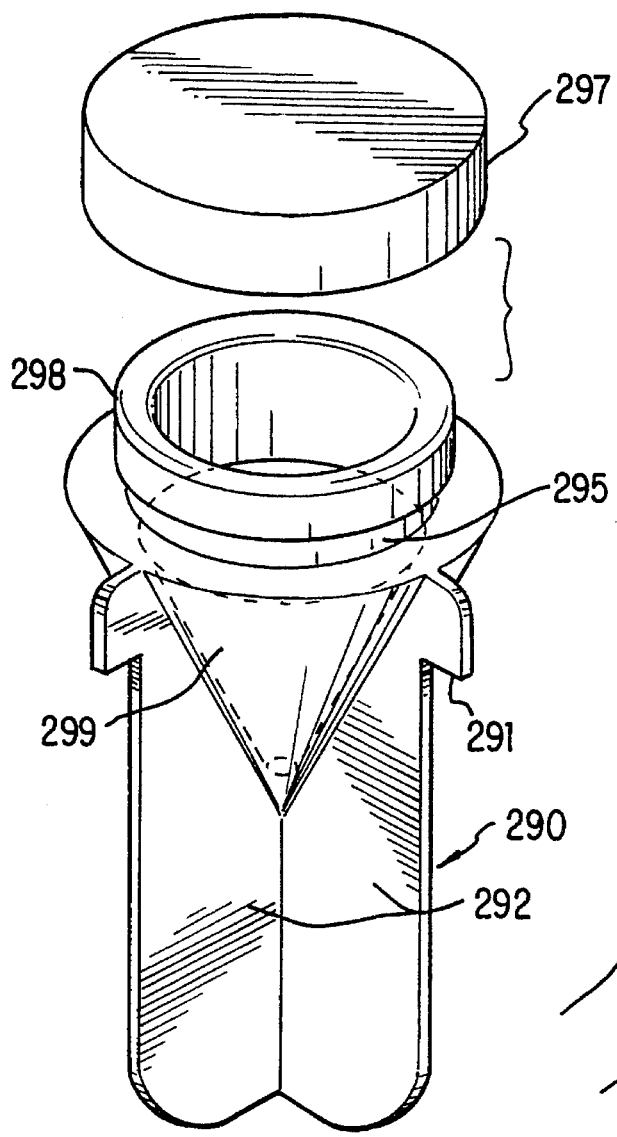

A presently contemplated, preferred embodiment of a container 224 is illustrated in FIGS. 13 and 14. The preferred embodiment eliminates the movable spout 40 of the first embodiment illustrated in FIGS. 2–12. Instead, the spout and collar are provided as a unitary, stationary structure or spout 240 attached to the container neck 241. In particular, the stationary spout 240 includes a base flange 238 disposed on a low density polyethylene gasket 234 on the annular end surface 237 of the container body neck. An aluminum ferrule 239 is crimped around the components to hold them in place.

Further, unlike the first embodiment illustrated in FIGS. 2–12, the preferred embodiment illustrated in FIGS. 13 and 14 does not include a frangible membrane insert (e.g., the insert 32 containing the frangible membrane 50 as illustrated in FIG. 2). The interior of the stationary spout 240 in the preferred embodiment illustrated in FIG. 13 communicates directly through the container body neck 241 with the liquid agent in the container 240.

A spring retainer 280 is press fit into an annular channel 284 at the bottom of the inside cylindrical wall of the spout 240. The retainer supports the bottom of a compression spring 294 which has a top end biased against the outwardly extending portions 291 of four crosswalls which define an internal plunger 290.

The top of the plunger 290 includes a valve member or head 296 surrounded by a reduced diameter neck or groove 295 for snap-fit engagement a sealing cap 297. The sealing cap 297 is preferably fabricated from low density polyethylene and is adapted to engage, and tightly seal against, an arcuate, concave outlet valve seat 298. The upper, peripheral edge of the sealing cap 297 has a convex, arcuate sealing surface for engaging the valve seat.

Preferably, the plunger 290 has a conical formation 299 extending from the tops of the walls 92 and converging inwardly of the sealing cap 298. This promotes flow of the liquid agent out of the container.

The interior, upper end of the spout 240 defines a thread 301 for threadingly engaging a thread 303 on an inwardly projecting, inner skirt of an overcap 342. The overcap 342 includes a downwardly projecting, outer skirt 344, and an annular gasket 346 is disposed between the inner and outer skirts to engage the annular end surface of the spout.

In order to fill the vaporizer, the overcap 342 is removed, and the container 224 is inverted to dispose the spout 240 within the vaporizer receiving station. The receiving station may have substantially the same structure as that described above with reference to FIGS. 5–12. The exterior of the spout 240 preferably includes a key or rib 354 for aligning with, and being received within, a mating groove or recess in the receiving station (e.g., groove 160 in FIG. 9). This permits a specific type of vaporizer to be used only with a specific type of container having the appropriate rib configuration.

Preferably, three ribs 354 are provided for being received in three grooves. The ribs and grooves are circumferentially spaced. The center of each rib and groove is 120° from the center of the other two ribs or grooves, respectively.

As the container 224 is moved into in the receiving station, and the sealing cap 297 on the Outlet valve member or head 296 of the container 224 engages the inlet valve boss 146 (visible in FIG. 7 wherein the boss 146 is shown engaged with the plunger 90 of the first embodiment of the container). The inlet valve spring 150 is preferably weaker than the container outlet valve spring 294. Accordingly, the inlet valve 132 opens first. When the inlet valve pin 136 abuts the bottom of the receiving station bore 104, further inward movement of the container 224 causes the container outlet valve cap 297 to be pushed away from the outlet valve seat 298 to open the container 224. The container 224 can be held in place until the liquid agent discharges from the container into the vaporizer. The maximum level of the agent in the vaporizer is determined by the location of the outlet of the container spout 240 in the same manner as with the first embodiment of the container spout 40 as described above with reference to FIG. 12.

Figure 15:
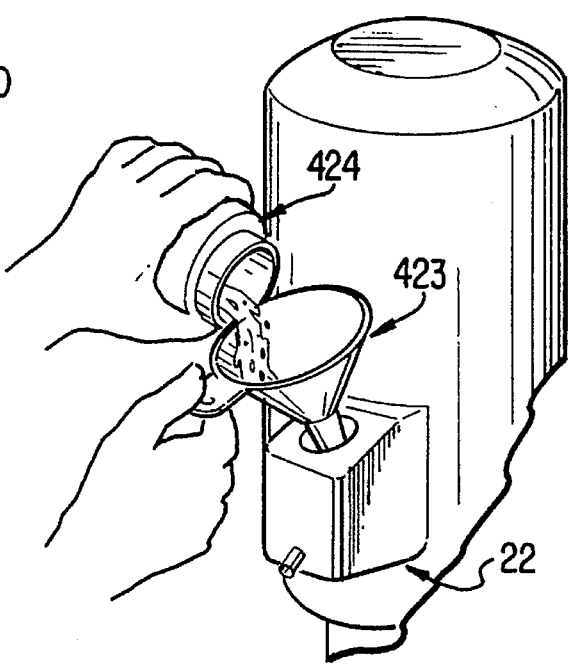
Figure 16:
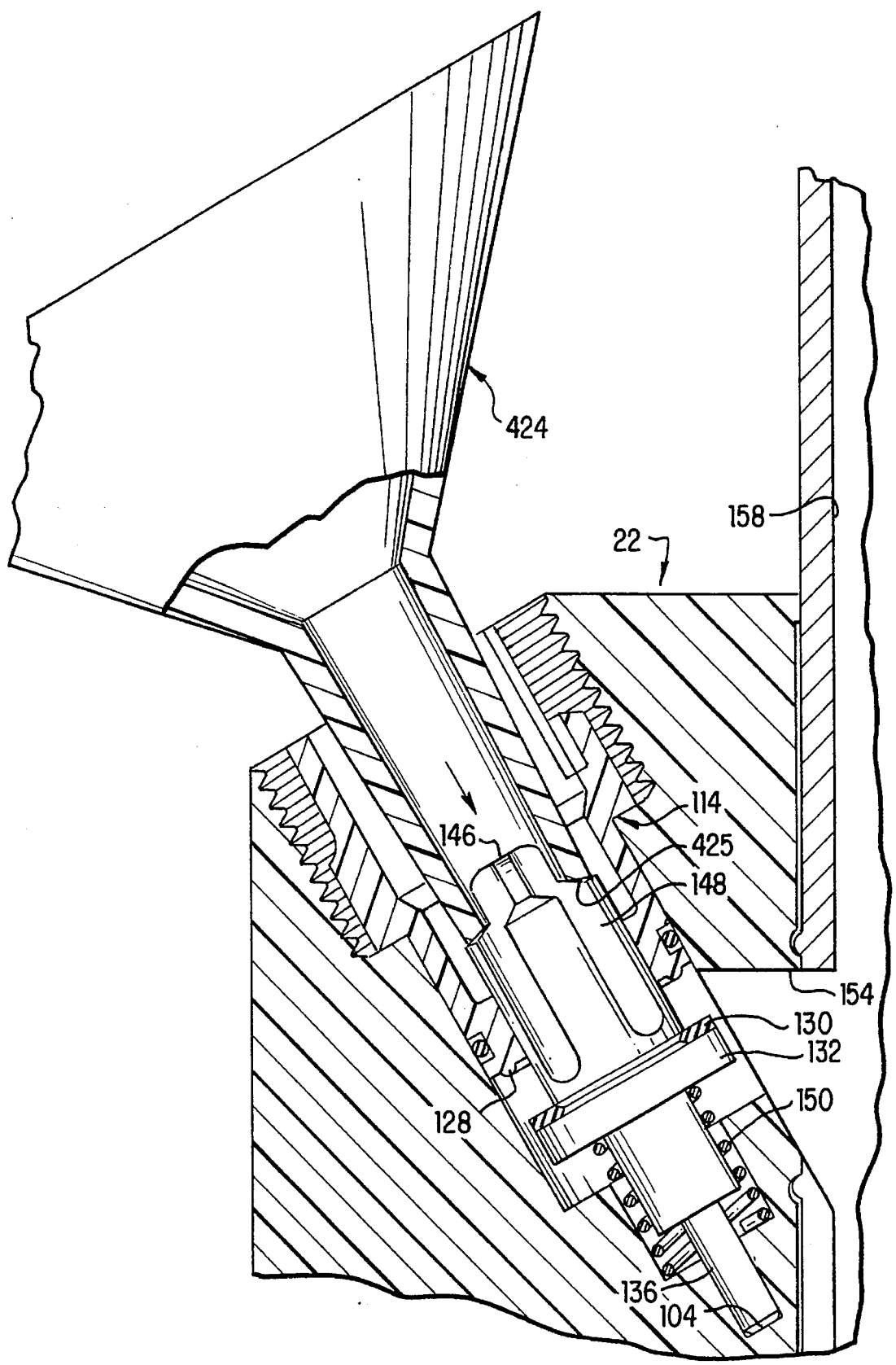

FIGS. 15 and 16 illustrate another form of a process for filling a vaporizer. In that process, a container 424 may be of a conventional type having a closure or cap which can be removed to permit discharge of the liquid anesthetic agent from the container. A funnel 423 can be inserted into the receiving station 22 and held therein while the liquid anesthetic agent is poured from the container 424 into the funnel 423.

As illustrated in FIG. 16, the lower, distal end 425 of the funnel 423 is sized to engage the engaging member 134 around the boss 146. The liquid agent can flow from the funnel 423 through the channels 148 in the fluted portion of the engaging member 134. The funnel 423 is pressed downwardly with sufficient force to overcome the inlet valve spring 150 so that the inlet valve member 132 is in the open condition spaced away from the annular sealing rib 128 on the stationary sleeve 114.

If desired, the funnel 423 can be provided with a special configuration having ribs or keys (not shown) for being received in the recesses 160 of the stationary sleeve 114. Funnels with other rib configurations could not be used with the vaporizer. The funnel with the appropriate rib configuration could be provided by the supplier of the particular liquid anesthetic agent and specific vaporizer. Thus, the operator would not be able to properly insert that specific ribbed funnel in a vaporizer having a different keying system. The operator would thus be less likely to attempt to fill some other type of vaporizer with that agent and associated ribbed funnel.

Figure 17:
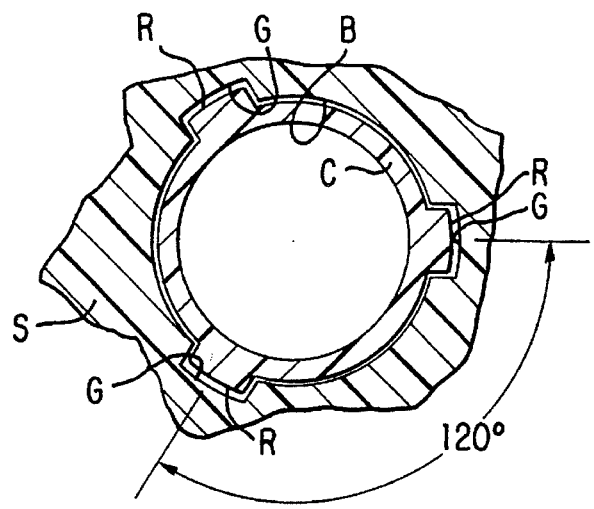
Figure 18:
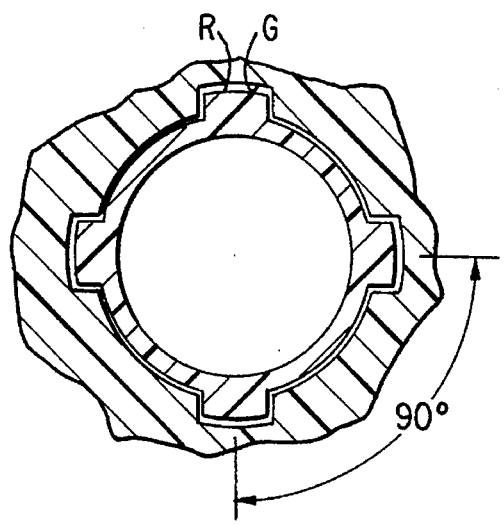

FIGS. 17–18 illustrate transverse cross-sections of various keying systems. FIG. 17 illustrates the preferred three-rib key system that can be employed in the embodiment illustrated in FIGS. 2–12 and in the embodiment illustrated in FIGS. 13 and 14. The ribs R are provided on a filling structure C, such as a container collar (FIGS. 2–12) or funnel spout (FIGS. 13 and 14). The center of each rib is 120° from the center of the other two ribs. Similarly, the mating grooves G within the mating sleeve S of the vaporizer receiving station are arranged so that the center of each groove is 120° from the center of the other two grooves.

Each rib R has two parallel side surfaces and a partially cylindrical outer surface connecting the two side surfaces. Each groove G has a corresponding mating configuration.

Preferably, the external radius of the spout or collar at the base of the ribs is 0.318 inch, and the internal radius of the cylindrical receiving passage or bore B within the stationary sleeve S in the receiving station is 0.324 inch. Further, the radius of the exterior circumferential surface of each rib R is preferably 0.371 inch, and the radius of the receiving groove G in the stationary sleeve is preferably 0.393 inch. The width of each rib is preferably 0.150 inch, and the width of each receiving groove is preferably 0.170 inch.

FIG. 18 illustrates an alternate embodiment for a rib structure in which four ribs are provided, each 90° apart. In a preferred embodiment, the sizes of the ribs and grooves are the same as described above with reference to FIG. 17.

Figure 19:
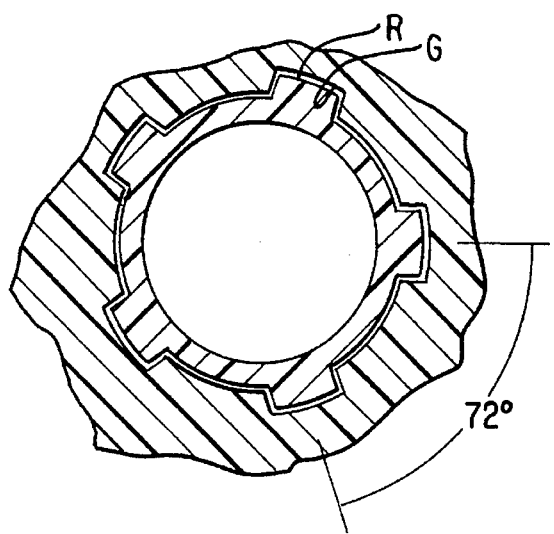

Another embodiment of a rib and groove key structure is illustrated in FIG. 19. Five ribs are located at 72° increments and are adapted to be received in mating grooves. In a preferred form, the sizes of the ribs and grooves are the same as described above with reference to FIG. 17.

Of course, if desired, the grooves could be provided in the container collar or funnel spout while the ribs could be provided on the receiving station.

It will be readily apparent from the foregoing detailed description of the invention and from the illustrations thereof that numerous variations and modifications may be effected without departing from the true spirit and scope of the novel concepts or principles of this invention.

What is claimed is:

1. A delivery system for delivery of a liquid anesthetic agent to an anesthetic vaporizer, said system comprising:

(A) an anesthetic agent supply container having a capacity to hold a liquid anesthetic agent, said container having a spout mounted thereon, said container having a stationary collar mounted thereon, said container further including a frangible membrane having a capacity to isolate the liquid anesthetic agent held in said container from an external environment of said container, said spout being movable lengthwise relative to said collar and said container between a first, extended position and a second retracted position, said spout having a proximal end portion having a capacity to rupture said frangible membrane when said spout is in said second, retracted position, said spout having a distal end portion constructed to engage a receiving station defined by the anesthetic vaporizer, said spout defining an outlet through which said agent can be discharged after said first end portion of said spout ruptures said frangible membrane.

2. The system in accordance with claim 1 in which a plurality of ratchet teeth are disposed on an exterior surface of said spout, and in which said collar has a pawl constructed to slide over said plurality of ratchet teeth when said spout is moved toward said first, extended position and constructed to engage one of said plurality of ratchet teeth to prevent movement of said spout toward said second, retracted position.

3. The system in accordance with claim 1 in which said container defines an outlet valve seat;

said container includes an outlet valve;

said outlet valve includes a sealing cap for engaging said outlet valve seat; and said sealing cap has a peripheral sealing surface for engaging said outlet valve seat.

4. The system in accordance with claim 3 in which said outlet valve seat is inwardly concave and arcuate;

said cap sealing surface is outwardly convex and arcuate; and said sealing cap is a separate structure snap-fitted onto an underlying support member.

5. The system in accordance with claim 4 in which said underlying support member is biased towards a closed position to urge said sealing cap against said outlet valve seat.

6. The system in accordance with claim 1 in which said container defines an annular end surface around said outlet;

internal threads are defined in said container adjacent said outlet; and said container includes an overcap with a threaded inner skirt for threadingly engaging said container threads.

7. The system in accordance with claim 6 in which said overcap includes an outer skirt; and said overcap includes a gasket disposed between said inner and outer skirts for sealingly engaging said annular end surface of the container around said outlet.

8. The system in accordance with claim 1 in which said container includes an inserted, annular retainer, a plunger adapted to move toward and away from the container outlet, and a compression spring having one end bearing against said insert retainer and another end bearing against said plunger for urging said plunger toward said outlet;

said plunger includes an outlet valve member; and said container defines an outlet valve seat against which said outlet valve is urged into sealing engagement by said spring.

9. The system in accordance with claim 8 in which said outlet valve member includes a sealing cap snap-fitted onto said plunger;

said sealing cap defines an outwardly convex, arcuate, peripheral sealing surface; and said outlet valve seat defines an inwardly concave, arcuate seating surface.

10. A delivery system for delivery of a liquid anesthetic agent to an anesthetic vaporizer, said system comprising:

(A) an anesthetic agent supply container defining an outlet through which said agent can be discharged;

(B) a valve seat in said container and a valve member in said container biased toward a closed position against said seat whereby flow through said outlet is occluded when said valve member is in said closed position; and (C) a cap removably attached to said container, said cap engaging said valve member and holding said valve member away from said valve seat to prevent contact between said valve seat and said valve member prior to removal of said cap.

11. The system in accordance with claim 10 in which said container includes a frangible membrane located inwardly of said container valve seat and said valve member, said membrane constructed to provide a liquid-tight seal and to isolate an interior of said container from an external environment of said container.

12. A delivery system for delivery of a liquid anesthetic agent to an anesthetic vaporizer, said system comprising:

an anesthetic agent supply container;

a receiving station on said anesthetic vaporizer for receiving said container so that said agent can be dispensed from said container into said vaporizer;

said container having a capacity to hold said liquid anesthetic agent, said container comprising a collar, a spout mounted within said collar and movable lengthwise between (1) an extended position and (2) a retracted position, and a frangible membrane located inwardly of said spout, said membrane constructed to provide a liquid-tight seal and to isolate said liquid anesthetic agent in said container from an external environment of said container;

said spout having a proximal end portion having a capacity to rupture said frangible membrane and having a distal end portion having a capacity to engage said receiving station to limit movement of said spout into said receiving station whereby said body and collar can continue to move relative to said spout after said distal end portion engages said receiving station to carry said membrane against said proximal end portion of said spout and rupture said membrane.

13. The delivery system in accordance with claim 12 in which said receiving station includes an inlet valve seat and an inlet valve member biased to seal against said inlet valve seat to occlude flow into said receiving station.

14. The system in accordance with claim 13 further including (1) an outlet valve seat defined by said spout and (2) an outlet valve member carried in said spout and biased to a closed position sealing against said outlet valve seat, said outlet valve member engagable with said inlet valve member to effect sequential opening initially of said inlet valve member and subsequently of said outlet valve member when said container is received in said receiving station.

15. A delivery system for delivery of a liquid anesthetic agent to an anesthetic vaporizer, said system comprising:

(A) an anesthetic agent supply container defining an outlet through which said agent can be discharged;

(B) an outlet valve member in said container and a first spring in said container biasing said outlet valve member to an extended, closed position occluding flow through said outlet;

(C) a receiving station on said anesthetic vaporizer for receiving said container and through which said agent can be dispensed into said vaporizer; and (D) a movable engaging member in said vaporizer receiving station and a second spring in said receiving station biasing said engaging member to an extended position from a fully depressed position, said engaging member being engagable with said valve member and being urged to said fully depressed position when said container is inserted into said vaporizer receiving station, said engaging member being restrained in said fully depressed position against further movement away from said extended position, and said second spring having less compression force than said first spring whereby said outlet valve member is moved away from said closed position by said engaging member only after said engaging member has been urged to said fully depressed position.

16. The delivery system in accordance with claim 15 in which said receiving station includes an inlet valve seat; and said engaging member includes an inlet valve member for sealing against said inlet valve seat to occlude flow into said receiving station when said engaging member is in said extended position.

17. A method for filling an anesthetic vaporizer with a liquid anesthetic agent, said method comprising the steps of:

providing a container holding a liquid anesthetic agent, said container having an outlet structure including an outlet valve and a frangible membrane sealing off communication between said liquid anesthetic agent held by said container and said outlet valve;

providing an anesthetic vaporizer having a receiving passage;

inverting said container holding said liquid anesthetic agent and disposing said container in said receiving passage in said vaporizer;

opening said outlet valve; and rupturing said frangible web whereby said agent can flow by gravity into said vaporizer.

18. The method in accordance with claim 17 further comprising the steps of providing an inlet valve in said receiving passage and opening said inlet valve in said receiving passage after said inlet valve engages said outlet valve.

19. The method in accordance with claim 17 further comprising providing a collar and a spout on said container, and wherein rupturing said frangible web comprises sliding said collar relative to said spout to engage said frangible membrane with said spout and rupturing said membrane with said spout.

20. A method for filling an anesthetic vaporizer with liquid anesthetic agent from a container, said method comprising the steps of:

providing a container of liquid anesthetic agent having a frangible membrane sealing the agent within said container and having an outlet through which the agent can be discharged by gravity flow upon rupture of said frangible membrane;

inverting said container in a receiving reservoir in said vaporizer; and rupturing said frangible membrane.

21. The method in accordance with claim 20 including the step of admitting ambient air from an external environment of the vaporizer into said container.

22. A method for filling an anesthetic vaporizer with a liquid anesthetic agent from a container of said agent, said method comprising the steps of:

providing a container of liquid anesthetic agent, said container having a hollow body containing said liquid anesthetic agent, a collar mounted on said body, a spout mounted within said collar, said spout being constructed to be movable lengthwise between an extended position and a retracted position, and a frangible membrane sealing said hollow body from an external environment of said container;

inverting said container of said liquid anesthetic agent and disposing said container in a receiving station in said vaporizer; and engaging said spout with said receiving station to limit movement of said spout into the receiving station whereby said body and collar can continue to move inwardly relative to said spout to carry said membrane against said spout and rupture said membrane.

23. A delivery system for delivery of a liquid anesthetic agent to an anesthetic vaporizer which has a receiving station with an engaging member projecting in the direction outwardly of said station, said system comprising:

an anesthetic agent supply container defining an outlet through which said agent can be discharged;

said container defining an outlet valve seat at said outlet;

said container including an outlet valve biased toward said seat, said outlet valve having a sealing cap having a capacity to engage said outlet valve seat, said sealing cap having a peripheral, outwardly convex, arcuate sealing surface for engaging said outlet valve seat; and said outlet valve defining a non-planar sealing surface for engaging said seat when said outlet valve is closed, said outlet valve being movable to an open position by engagement with said engaging member in said vaporizer.

* * * * *